US006264616B1

(12) United States Patent
Don

(10) Patent No.: US 6,264,616 B1
(45) Date of Patent: *Jul. 24, 2001

(54) ACOUSTIC TUMOR DETECTION USING STACKED DERIVED-BAND ABR AMPLITUDE

(75) Inventor: Manuel Don, Anaheim, CA (US)

(73) Assignee: House Ear Institute, Los Angeles, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/562,052

(22) Filed: May 1, 2000

Related U.S. Application Data

(63) Continuation of application No. 09/079,411, filed on May 13, 1998, now Pat. No. 6,080,112.

(51) Int. Cl.[7] ....................................................... A61B 5/00
(52) U.S. Cl. ............................................................... 600/559
(58) Field of Search .................................... 600/544, 545, 600/559

(56) References Cited

PUBLICATIONS

"Electrocochleography and Auditory Brainstem Electric Responses in Patients with Pontine Angle Tumors", *Ann. Otol Rhinol Laryngol* 1980; 89 (suppl 75):1–19, J.J. Eggermont, M. Don, and D.E. Brackmann.

"Efficacy of Auditory Brainstem Response as a Screening Test for Small Acoustic Neuromas", *Am J Otol* 1995; 16:136–139 by M.L. Gordon and N.L. Cohen.

"The Auditory Brain Stem Response I–V Amplitude Ratio in Normal, Cochlear, and Retrocochlear Ears", *Ear Hear* 1984; 5:52–55, Musiek, Kibbe, Rackliffe, et al.

"Quality Estimation of Averaged Auditory Brainstem Responses", Elberling C., Don M., *Scand Audiol* 1984; 13:187–197.

"Evaluating Residual Background Noise in Human Auditory Brainstem Responses", Don M., Elbelring C., *J. Acoust Soc Amer* 1994; 96:2746–2757.

"Estimation of Auditory Brainstem Responses, ABR, by Means of Bayesian Reference", Elberling C., Wahlgreen D., *Scand Audiol* 1985; 14:89–96.

*Primary Examiner*—Max Hindenburg
(74) *Attorney, Agent, or Firm*—Blakely, Sokoloff, Taylor & Zafman LLP

(57) ABSTRACT

A diagnostic procedure first records a patient's auditory brainstem response (ABR) to each of a plurality of auditory stimuli. The stimuli comprise 60 dB nHL clicks using high pass noise masking procedures to isolate the cochlear response within specific frequency bands. These derived band ABRs are temporally shifted to align the wave V peak amplitudes. The time-shifted responses are then summed to create the stacked ABR. The stacked wave V ABR amplitude is compared to a threshold value. The stacked wave V ABR amplitudes for patients having small (less than or equal to 1 cm.) intracanalicular tumors are measurably lower than those for otherwise similar individuals without tumors.

8 Claims, 16 Drawing Sheets

ACOUSTIC TUMOR DETECTION USING STACKED DERIVED-BAND ABR AMPLITUDE

This application is a continuation of Ser. No. 09/079,411 filing date May 13, 1998 now U.S. Pat. No. 6,080,112.

BACKGROUND OF THE INVENTION

1. Field of the Invention

This invention relates generally to the field of acoustic tumor detection. More particularly, the invention relates to a diagnostic technique for detecting small ($\leq 1$ cm) intracanalicular tumors.

2. Prior Art

Until recently, the auditory brainstem response (ABR) test was an important component of the clinical test battery for acoustic neuromas. Early studies reported detection in the 95% –98% range, but these tumors were typically fairly large. In "Electrocochleography and Auditory Brainstem Electric Responses in Patients with Pontine Angle Tumors", *Ann Otol Rhinol Laryngol* 1980;89 (suppl 75):1–19, J. J. Eggermont, M. Don, and D. E. Brackmann examined the impact of tumor size on detection using estimates from CT scans and surgical reports and concluded that tumors smaller than 1.0 cm often go undetected by standard clinical ABR methodology. This conclusion has been supported by more recent and extensive studies that compared the sensitivity of this ABR methodology with gadolinium (Gd-DTPA) enhanced magnetic resonance imaging (MRI). Using standard measures of peak and inter-peak latencies, waveform morphology, or presence of waves, the ABR tests were nearly 100% accurate in detection of all extra- and intracanalicular tumors larger than 1.0 cm. However, for intracanalicular tumors smaller than 1.0 cm, the accuracy of some of these standard latency measures varied across studies from 63% to 93% with corresponding false negative rates ranging from 7% up to 37%. This wide range of detection and false positive rates is probably due to the different criteria selected. The high failure rate in detecting small intracanalicular tumors in some of these studies is not surprising since normal ABR latencies are possible if they are determined by a frequency region of the cochlea not affected by the tumor. Possible mechanisms underlying latency changes caused by tumors have been discussed and reviewed in "Efficacy of Auditory Brainstem Response as a Screening Test for Small Acoustic Neuromas", *Am J Otol* 1995; 16:136–139 by M. L. Gordon and N. L. Cohen.

ABR Methodology

Two of the most widely used ABR latency measures for tumor detection, the $IT_5$ (Inter-aural Time for wave 5) and I–V interpeak delay, are illustrated in FIG. 1. The top trace represents a standard ABR from a normal-hearing non-tumor ear; the lower trace, the response from an ear with a tumor. The $IT_5$ is the wave V latency difference between ears of the same subject. If the difference is greater than 0.2 ms after compensating for hearing loss, the test is positive for a tumor. While this criterion has been effective in detecting tumors larger than 1.0 cm, its sensitivity to smaller tumors is only about 80%. Furthermore, the $IT_5$ should not be used when bilateral tumors are suspected, as in Neurofibromatosis II (NF2) cases, or if the non-suspect ear has a greater than moderate degree of hearing loss and poor ABRs. Thus, this measure is most useful in detection of unilateral tumors when there is relatively little impairment of the non-suspect ear.

The other latency measures illustrated in FIG. 1 are the interpeak delays between waves I and V and between waves I and III of the ABR from the ear suspected of a tumor. In males, the I–V delay is normally about 4.2 ms and the I–III delay is about 2.1 ms; in females the delays are slightly shorter. The advantage of these delay measures is that they are intra-aural; thus, it is not necessary to consider the hearing status of the subject's non-suspect ear. If the delays are abnormally long, the test is positive and a tumor is suspected. The accuracy of these measures depends on the definition of "abnormally long". Some studies used two or three standard deviations from the mean for normal-hearing subjects, while others used a specific delay, e.g. I–V delay of 4.4 ms or greater. Many of these studies have shown that small intracanalicular tumors are difficult to detect using latency measures. The major problem in measuring inter-peak delays is the difficulty of recording wave I in patients with tumors or high frequency hearing losses. Other latency measures, such as the inter-aural rather than the intra-aural I–V delay and latency-intensity functions, have also been examined.

ABR latencies are typically used in clinical applications because they are robust measures. By definition, a robust measure tends to be insensitive to small perturbations. Thus, it is not too surprising that robust latency measures are insensitive to the small neural perturbations caused by small tumors. A more detailed explanation of this insensitivity is presented below.

Consequence of ABR Insensitivity to Small Tumors

Since many studies have demonstrated the inadequacy of standard ABR measures in detection of tumors smaller than 1.0 cm, clinical practice has shifted to using MRIs. Gd—DTPA MRIs have now replaced contrast computed tomography (CT) as the "gold standard" in diagnosis of acoustic tumors. MR imaging does not use ionizing radiation and provides greater soft tissue contrast which improves differentiation of tumor from surrounding bone, spinal fluid, and brain. In addition, Gd—DTPA MRI provides reliable identification, size, and location of tumors as small as 3.0 mm in the internal auditory canal region.

Unfortunately, due to the low incidence of acoustic tumors even in cases with clinically significant signs, many patients without tumors are imaged. Changes in the health care delivery system now place a heavy emphasis on cost reduction and justification of expensive medical tests.

One approach to reducing MRI costs involves reduced field studies in which a limited number of slices are taken through only the cerebellopontine angle (CPA), thereby excluding the rest of the brain. Typically, the requests for these limited studies are very specific and not of a general screening nature. While this approach risks overlooking other lesions of the intracranial vault because of the limited field of view, a number of other specialties that rely on imaging perform limited studies without undue concern about the medical-legal liability of missing nearby lesions. This concept of limited studies could be a viable alternative to the full MRI when specifically searching for a mass lesion of the CPA.

A second approach, using new surface coils technology capable of rapid data acquisition and faster studies, appears to have good sensitivity. The faster studies result in shorter scanning time and, therefore, less cost to the patient. However, this faster technology requires major software and hardware upgrades for older systems. If upgrades are possible, the cost may be as much as $1,000,000. Newer systems are easier to upgrade and have incorporated hardware that reduces the scanning noise of fast acquisition studies. The availability and distribution of these new faster systems are unknown.

Patient-related problems sometimes limit the usefulness of the MRIs. For example, many individuals cannot tolerate the claustrophobic confines of the scanner. Some of these individuals may require extraordinary measures such as sedation to even attempt an MRI. Others are simply too large to fit into the MRI machines. Open MRI systems may reduce these problems, but currently the resolution of these systems is sub-optimal for detecting small acoustic tumors. In addition, some individuals may have metal (such as pacemakers) in their bodies that cannot be exposed to the magnetic field. Finally, small communities may not have access to an MRI device. The cost and inconvenience to travel long distances to an imaging center may be problematic for some patients.

The emphasis on medical cost containment may require additional justification for requesting an expensive imaging test. A significant inroad to medical cost containment and justification could be achieved by an improved ABR methodology that detects small acoustic tumors with high sensitivity and acceptable specificity. Standard ABR techniques are relatively inexpensive, non-invasive, non-threatening, and widely available.

The Search for Another ABR Measure

If latency is often insensitive to the effects of small tumors, what about other parametric measures of ABRs? Over the years, many studies examined ABR amplitude measures and concluded that they are often too variable when compared to latencies. However, amplitude measures should be very sensitive to loss or desynchronization of eighth nerve activity due to compression by an acoustic tumor. In "The Auditory Brain Stem Response I–V Amplitude Ratio in Normal, Cochlear, and Retrocochlear Ears", *Ear Hear* 1984; 5:52–55, Musiek, Kibbe, Rackliffe, et al. used wave V to wave I amplitude ratios and found that low ratios (less than 1) indicated the presence of a tumor; normal-hearing and cochlear lesion patients seldom had ratios lower than 1. However, only 44% of the tumors were detected in this manner. Other problems with these amplitude ratios are: 1) they are dependent on the presence of wave I; 2) they may be more sensitive to variations in the audiometric configuration because the amplitude of wave I is more dependent than wave V on higher frequency regions of the cochlea; and 3) using a ratio of two measures that are highly variable results in an even more highly variable measure.

SUMMARY OF THE INVENTION

Before amplitude measures can be used clinically, their variability must be addressed and resolved. Two major contributors to this amplitude variability are the residual noise in the average and variations in the response times across the cochlea. The procedure of the present invention implements measures to control and estimate the amount of residual noise. In addition, the present invention utilizes a method for reducing the effects of variations in response times across the cochlea. This method creates what is referred to herein as a "stacked ABR". By controlling the amount of residual noise in the ABR waveform and by using wave V amplitude measures of the stacked ABR, small tumors missed by standard ABR latency measures can be detected.

The procedure of the present invention first records the patient's ABR to each of a plurality of auditory stimuli. The stimuli comprise 60 dB nHL clicks using high pass noise masking procedures to isolate the cochlear response within specific frequency bands. These derived band ABRs are temporally shifted to align the wave V peak amplitudes. The time-shifted responses are then summed to create the stacked ABR. The stacked wave V ABR amplitude is compared to the mean stacked wave V ABR amplitude for normal hearing individuals of the same gender as the patient. The stacked wave V ABR amplitudes for patients having small ($\leq 1$ cm.) intracanalicular tumors are significantly lower than those for normal hearing individuals without tumors.

Even greater specificity is achievable by comparing the stacked wave V ABR of a patient to the mean stacked wave V ABR amplitude for individuals having a comparable degree of cochlear hearing loss. Specificity can also be improved by comparing the stacked wave V ABR amplitudes of the two ears of a patient, i.e., using a patient's non-tumor ear as a control to diagnose the presence of a tumor in the other ear. Experimental results have shown that stacked ABR losses due to tumors are additive to other causes of cochlear hearing loss.

The time needed for data collection depends on the patient's level of relaxation, but 15–20 minutes are typically required for completion. The analysis takes another 15 minutes (and can be done after the patient leaves). Thus, since the stacked ABR technique requires relatively inexpensive upgrading of existing ABR systems, this new improved methodology can serve as a cost-efficient screening measure for imaging requests.

The stacked ABR wave V amplitude measure used in the present invention is sensitive to small intracanalicular tumors with good specificity relative to normal-hearing non-tumor individuals. The clinical benefits of a reliable ABR measure sensitive and specific to small acoustic tumors are 1) lower costs for detecting a tumor by decreasing the number of non-tumor cases referred for imaging, 2) widespread accessibility of a test that incurs relatively little additional hardware or software costs over standard ABR methods, 3) an alternative test for those not suited for MR imaging, and 4) an objective means to justify a request for MR imaging.

DETAILED DESCRIPTION OF THE INVENTION

In the following description, for purposes of explanation and not limitation, specific details are set forth in order to provide a thorough understanding of the present invention. However, it will be apparent to one skilled in the art that the present invention may be practiced in other embodiments that depart from these specific details. In other instances, detailed descriptions of well-known methods and devices are omitted so as to not obscure the description of the present invention with unnecessary detail.

Diagnostic Procedure

Figure 15:
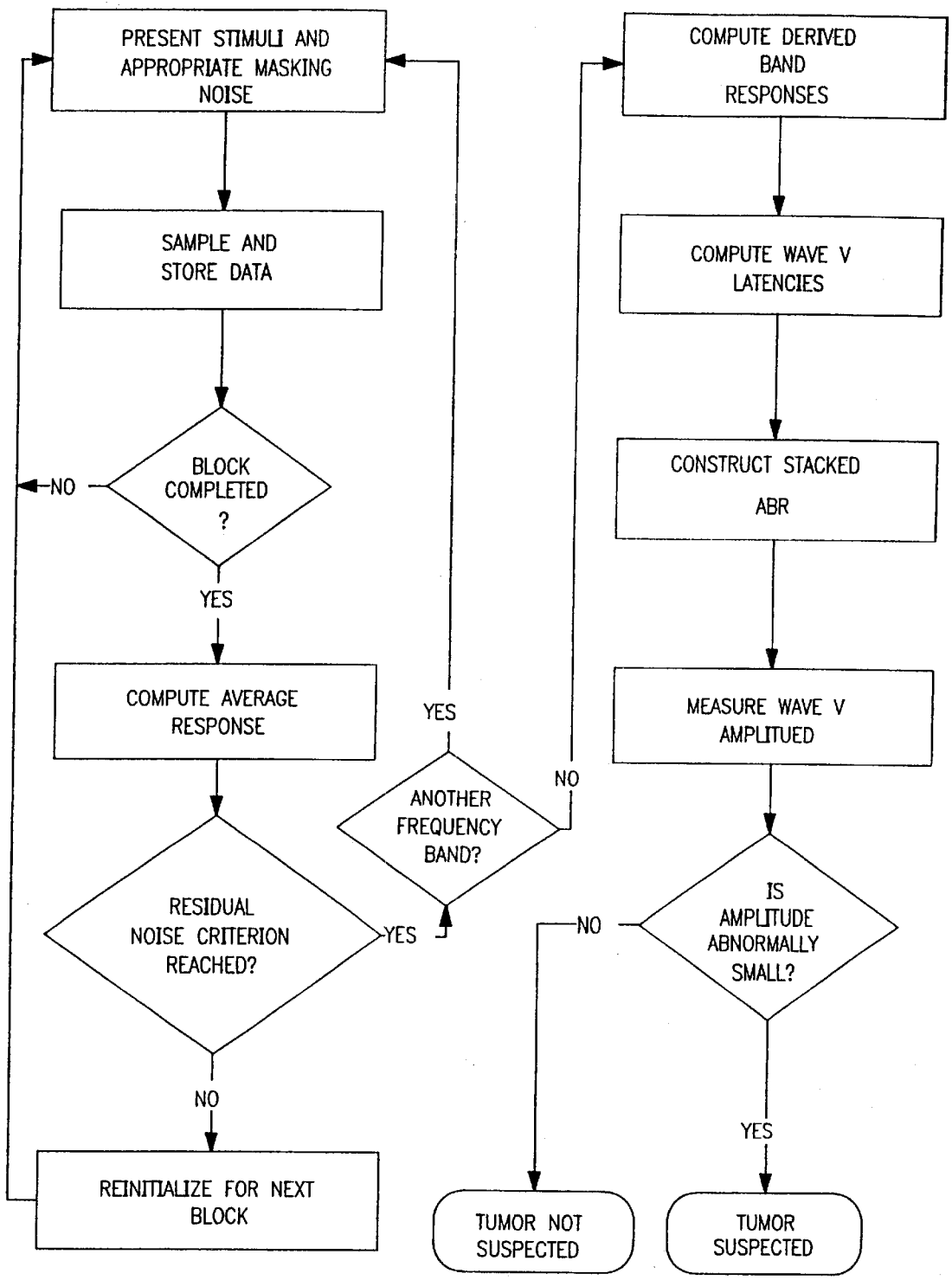
FIG. 15 is a functional flow diagram illustrating the diagnostic procedure of the present invention.

The diagnostic procedure of the present invention is summarized in the flow chart of FIG. 15. Each of the procedural steps is described in detail below.

Patient Screening and Preparation

Prior to conducting the diagnostic procedure of the present invention, patients are subjected to audiometric tests to rule out existing conductive impairment. Air and bone conduction audiometry is administered for at least 0.5 kHz, 1 kHz, 2 kHz, 4 kHz and 8 kHz. Preferably, results are also obtained for 0.75 kHz, 1.5 kHz, 3 kHz and 6 kHz. Patients are also screened for middle ear problems with tympanometry. If a middle ear or conductive impairment is found, it must first be resolved before diagnostic results using the present invention can be meaningfully interpreted.

Patients are placed in a reclining chair or bed in a double-walled sound-treated room (IAC). The room should be appropriately shielded and grounded to minimize electrical artifacts. ABRs are recorded differentially between electrodes applied to the vertex (Cz) and the ipsilateral mastoid (M1 or M2). The impedance of each electrode at 1 kHz should be less than 5 k ohms. The contralateral mastoid is used as ground.

Stimuli

The auditory stimuli are rarefaction clicks produced by applying 100 $\mu$s rectangular voltage pulses to TDH-49, TDH-50P or equivalent earphones. Clicks are presented 22 ms apart at 93 dB peak-peak equivalent sound pressure level (p.-p.e. SPL) with 1 kHz tone as the reference. The acoustic clicks are calibrated and measured with a Brüel and Kjaer 4152 artificial ear, 6 cc coupler, and 2209 sound level meter. For normal hearing individuals, 93 dB p.-p.e. SPL is 63 dB above the average perceptual detection threshold.

Ipsilateral pink-noise masking is used to obtain derived ABRs. The noise is produced by a General Radio Noise Generator (Type 1310) and presented at a level sufficient to mask the ABR to the clicks. For the 93 dB p.-p.e. SPL clicks, the required broad-band pink-noise RMS level is 92 dB SPL. There are six stimulus conditions: clicks presented alone (unmasked condition) and clicks presented with ipsilateral noise high-pass filtered (slope=96 dB/octave) at 8, 4, 2, 1, and 0.5 kHz. The high-pass filtering of the masking noise is achieved by cascading both channels of a Krohn-Hite (Model 3343) dual filter, each with a 48 dB/octave slope.

Data Acquisition

The patient's scalp activity is amplified by $5 \times 10^5$ and filtered (cascading two Princeton Applied Research Model 113). Filtering is Butterworth type with a passband of 0.1 to 3 kHz and roll-off slopes of 12 dB/octave. The activity is sampled at a rate of 20 kHz for 15 ms after stimulus onset with use of an Ariel DSP-16 A/D–D/A board (or equivalent) and a PC computer. This is equivalent to 300 data samples per sweep for each stimulus presentation.

The DSP analysis window is set to span from 1 to 11 msec. The artifact reject level is set just below the voltage clipping level of the A/D converter. Any sweep in which a single data point within the analysis window exceeds the rejection level is rejected. Accepted digitized sweeps are stored in a buffer and the converted value at 6 msec after stimulus onset (data point 120) is stored in a separate buffer.

After each block of 256 sweeps, the RMS value of the averaged background noise is estimated using the 256 data points collected at 6 msec into each sweep. The noise estimation procedures are described in "Quality Estimation of Averaged Auditory Brainstem Responses", Elberling C., Don M., *Scand Audiol* 1984; 13:187–197 and in "Evaluating Residual Background Noise in Human Auditory Brainstem Responses", Don M., Elberling C., *J. Acoust Soc Amer* 1994; 96:2746–2757.

A Bayesian estimation weighting scheme is implemented to form an average response in which each block of 256 sweeps is weighted inversely to the estimated residual noise in the average of the block of sweeps. The weighting technique is described in "Estimation of Auditory Brainstem Responses, ABR, by Means of Bayesian Reference", Elberling C., Wahlgreen D., *Scand Audiol* 1985; 14:89–96. This technique removes the need to vary the artifact rejection level and reduces the destructive effects of physiological background noise variation on the ABR average by weighting the average towards those blocks of sweeps with low estimated background noise.

Data collection for a run is terminated when the estimated residual background noise in the average reaches 20 nanovolts (nV) or less. Thus, all recordings have low and approximately the same estimated residual background noise levels. The use of residual background noise level as the stopping criterion rather than a fixed number of sweeps reduces the substantial effect of physiological background noise variation on the interpretation of the ABR recordings.

Data Analysis

Figure 1:
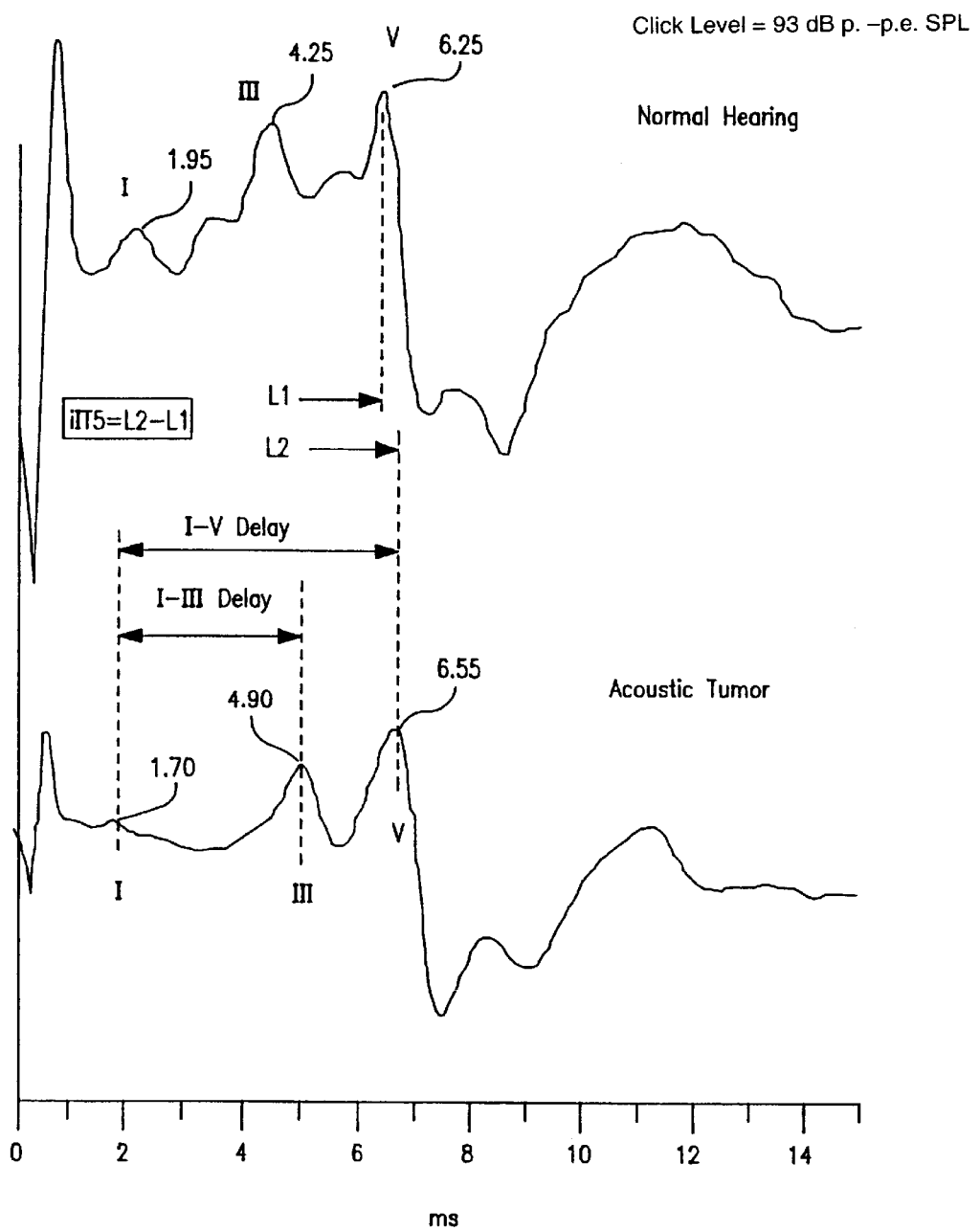
FIG. 1 illustrates prior art standard ABR measures used for acoustic tumor detection.
Figure 2:
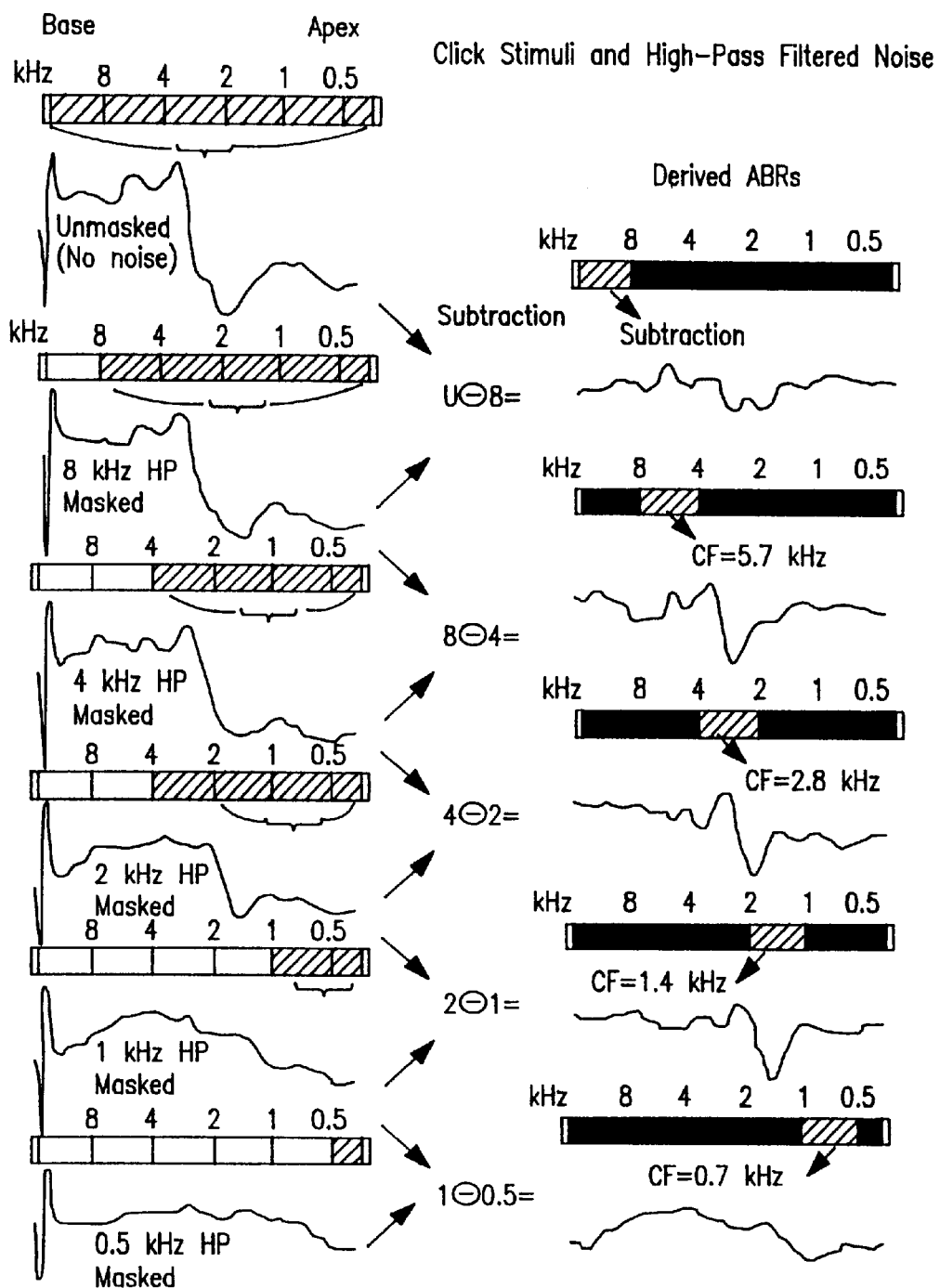
FIG. 2 is a schematic illustration of the high pass noise masking technique used to obtain derived band ABRs with the present invention.

The derived narrow-band ABR technique consists of the simultaneous ipsilateral presentation of a broad-band click and high-pass filtered noise. The portion of the cochlea that is masked by the high-pass noise does not contribute to the ABR. The cut-off frequency of the high-pass noise is successively lowered from one run to the next. Narrow-band contributions from the cochlea are then derived by successive subtraction of the responses to the successive high-pass noise masking conditions. This method for generating a series of derived ABRs is shown in detail in FIG. 2. At the top of the left side of the figure is a schematic representation of the cochlea with its various frequency regions delineated. Directly below the schematic cochlea is the standard unmasked ABR response to click stimuli alone. Because of the broad spectrum of click stimuli, this response is initiated by stimulation of the whole cochlea (light area with wavy lines in the schematic cochlea). The second schematic cochlea on the left side of FIG. 2 is paired with the ABR response to clicks with ipsilateral high-pass noise masking the region of 8 kHz and above (shaded region with M label in the schematic cochlea). Since the cochlear region of 8 kHz and above is masked by the noise, this ABR represents activity that is initiated from regions below 8 kHz. When this second response is subtracted from the unmasked response (encircled minus sign), the result is the derived response shown as the top waveform on the right side of FIG. 2. The schematic cochlea above this derived response shows that the activity is initiated from a region of the cochlea above 8 kHz. This process is repeated by masking progressively lower frequency areas of the cochlea (see the last four schematic cochleae paired with their responses on the left side of the figure) and subtracting the resulting response from the previous one to form the derived response shown immediately to the right (along with its schematic cochlea). This procedure results in five derived-band ABRs representing activity initiated from regions of the cochlea approximately one octave wide (responses and schematic cochleae on right side of FIG. 2). Each of the derived-band responses are smoothed with a 3-point smoothing algorithm to further reduce residual high-frequency noise in the average response. The theoretical center frequency (CF) for each derived band is computed as the square root of the product of the two successive high-pass filter cut-off frequencies used to form the band. Thus, the theoretical CFs of the derived bands are 11.3, 5.7, 2.8, 1.4, and 0.7 kHz.

Figure 3:
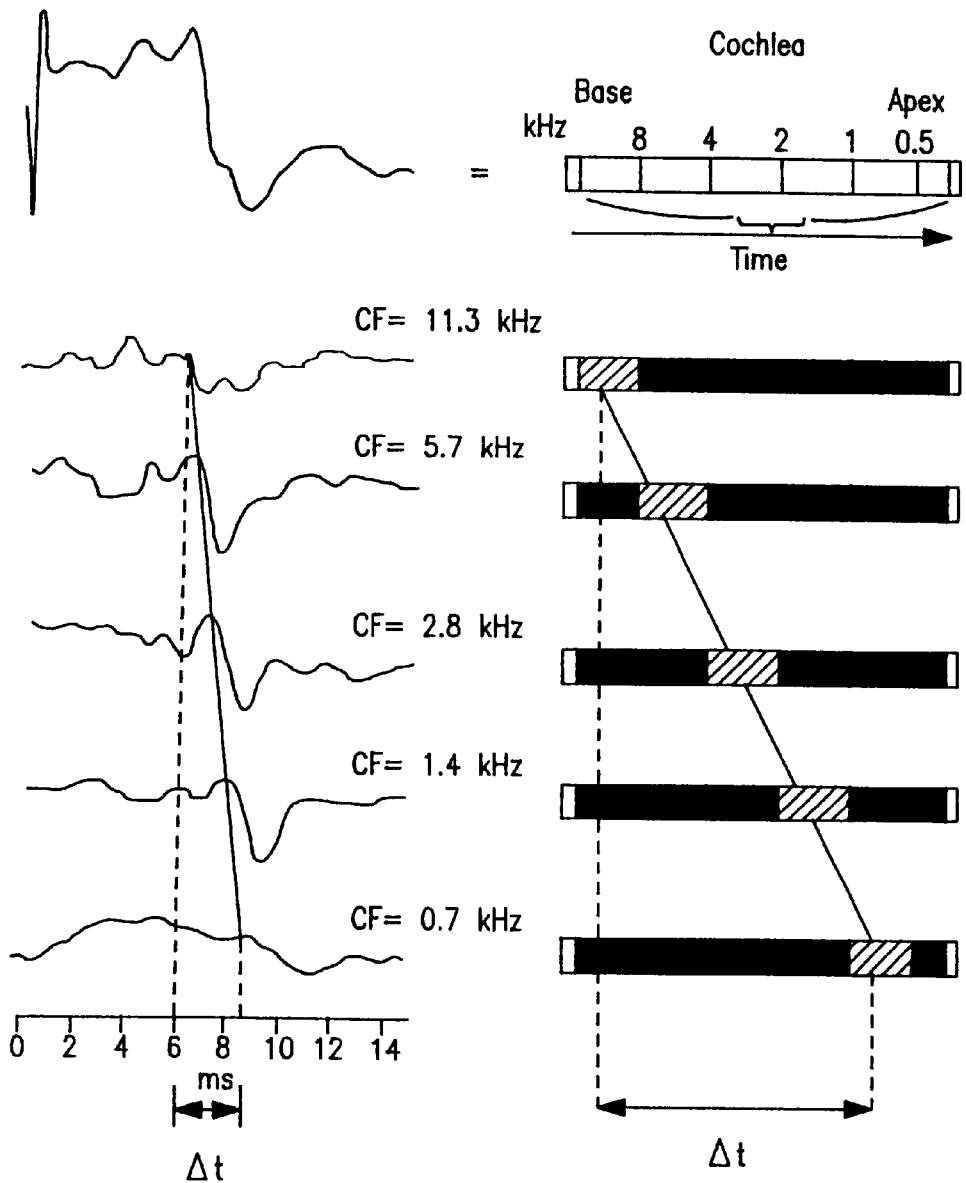
FIG. 3 illustrates the manner in which derived band ABRs are influenced by the time delay while traversing high to low frequency regions of the cochlea.

The standard unmasked and derived ABRs are replotted in FIG. 3. Basically, the standard unmasked ABR is the temporally unaltered sum of activity initiated from all of the cochlea represented by the five derived bands plotted below it. As shown in this figure, wave V latencies are longer for each successive (lower-CF) derived ABR. These latencies reflect the cochlear response time composed of an apparent traveling-wave delay and a frequency-dependent synchronization time. The delay in peak activation ($\Delta t$) from different regions of the cochlea demonstrates that the activity of the cochlea underlying the generation of the ABR is not totally synchronous in time. This delay in response times across the cochlea has been found to be less in females than males and may be related to the shorter basilar membrane in females.

In addition, variations in cochlear response times between individuals are partially responsible for variations in wave V amplitude between individuals. For example, the amplitude of wave V in the unmasked response (top trace, left side of FIG. 3), will vary depending on the wave V time delay ($\Delta t$) between the derived bands (remaining traces, left side of FIG. 3) that compose the unmasked response. Variations in the delay ($\Delta t$) alter the degree of synchrony of the activity between the different regions of the cochlea, which in turn affects the amplitude of wave V. To minimize this influence of cochlear response time on amplitude measures, the stacked ABR method was developed.

Figure 4:
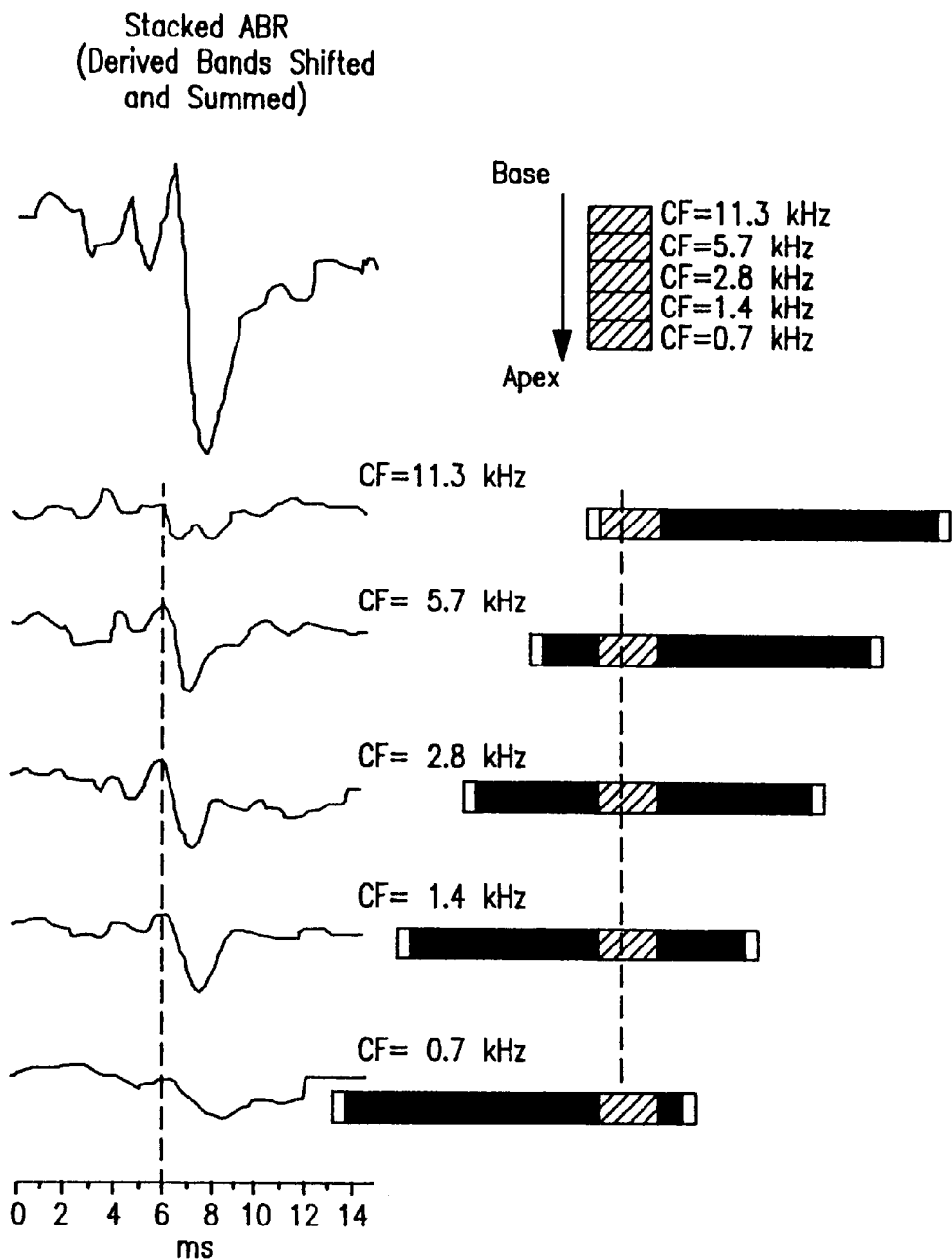
FIG. 4 illustrates the temporal shifting of derived band ABRs to create the stacked ABR.
Figure 5:
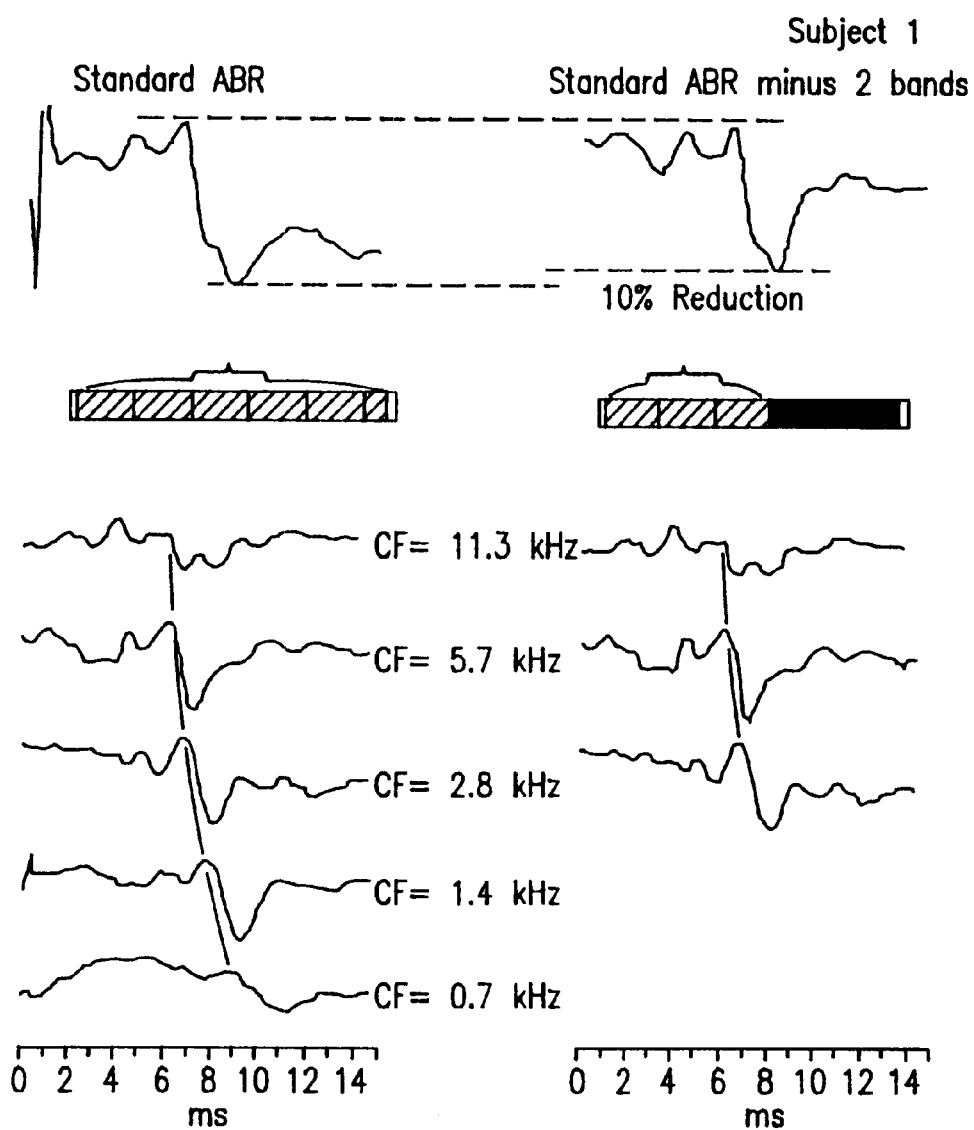
FIG. 5 illustrates the lack of sensitivity of the standard ABR to loss of contributions from low frequency cochlear regions in a normal hearing subject.
Figure 8:
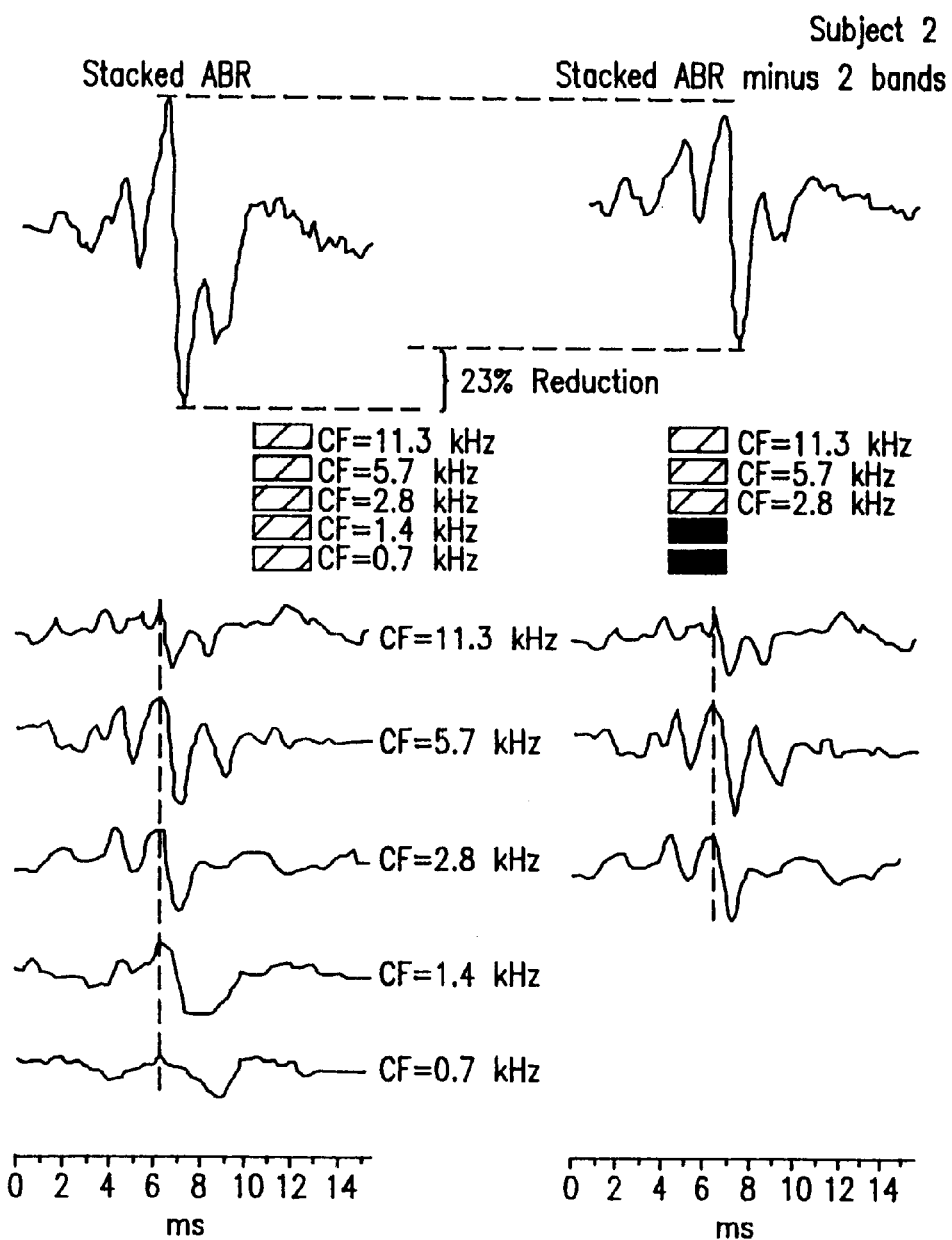
FIG. 8 illustrates the stacked ABR amplitude with low frequency bands removed for the same subject as shown in FIG. 7.

FIG. 4 illustrates the construction of a stacked ABR from the derived bands in FIG. 3. The stacked ABR is constructed by (1) time shifting the derived-band waveforms so the peak latencies of wave V in each derived band coincide, and (2) adding together these shifted derived-band waveforms. Arbitrarily, the wave V peaks of the derived bands are aligned to the wave V peak latency for the 5.7 kHz derived band. If no wave V is discernible in the 5.7 kHz derived band, any of the other derived-band responses with a discernible wave V may be used as the reference wave form for aligning the others. Any derived-band wave form without a discernible wave V is not time-shifted. The top trace in FIG. 4 is the stacked ABR representing the sum of the temporally aligned derived bands shown below it. By temporally aligning the peak activity initiated from each segment of the cochlea, the total cochlear activity has been synchronized. Thus, as a first approximation, the amplitude (peak to succeeding trough) of the stacked ABR wave V reflects more directly the total amount of cochlear activity. than an expected decrease, occurs because the peak response times of these two lowest derived bands phase cancels some of the peak activity generated by the other bands. Thus, when this phase canceling activity is removed, the standard ABR wave V amplitude appears to increase. However, when the stacked ABR amplitude method is applied to this subject's data, the expected amplitude decrease is observed. This is shown in FIG. 8 (right side) where removal of the two lowest bands produces a 23% reduction in the stacked ABR wave V amplitude. In essence, stacked ABR wave V amplitudes minimize, to a large extent, the confounding effects of phase cancellation of activity resulting from variations in cochlear response times. As a result, the stacked ABR wave V amplitude is more sensitive than the standard wave V amplitude measures to a small reduction in or desynchronization of auditory neural activity that may result from compression by a small tumor. The stacked ABR wave V amplitude is also more sensitive than wave V peak latency measures.

Experimental Results

Normal-Hearing Non-Tumor Control Group

Patients with small (<1 cm) tumors can have normal hearing. Any new methodology must first clearly distinguish between normal-hearing non-tumor ears and those with small tumors. Therefore, a control group of normal-hearing subjects in good general health and reported normal neurological status was tested. Otoscopic examinations were performed to identify existing conditions that would preclude audiometric and ABR testing. At the time of ABR data collection, pure-tone audiometric testing was performed with a Grason-Stadler GSI 16 audiometer and Telephonics TDH 50P earphones. Hearing thresholds were evaluated in 2 dB steps using the modified Hughson-Westlake procedure. Normal hearing was defined as pure-tone thresholds of 10 dB or less for frequencies between 500 to 4000 Hz; 15 dB or less for 6000 and 8000 Hz.

Acoustic Tumor Patients

The test population for this study was restricted to patients who had clinical complaints related to hearing or balance, a Gd—DTPA MRI indicating presence of a tumor, and surgical confirmation of the tumor (the largest was 2.2 cm in its longest dimension). The first restriction is important because individuals without symptoms would normally not be clinically evaluated. The major exceptions are patients at risk for Neurofibromatosis Type II (NF2). These patients are tested and imaged whether or not they have clinical signs. NF2 patients without clinical signs were excluded from the study. A total of 24 patients and 25 ears were tested.

Standard ABR Latency Measures

For each control subject and tumor patient tested, the I–V latency delay was measured. $IT_5$ was also measured in all tumor patients except for patients with known or suspected NF2 and, therefore, possible bilateral tumors. The $IT_5$ was also not used if there was little or poor hearing in the non-tumor ear. Five of the 25 confirmed tumors cases went undetected by standard ABR latency analyses. This yielded a detection or sensitivity rate of 80% which is consistent with previous work on larger populations. For these five cases, the patient's gender, clinical symptoms, ear with the tumor, estimated tumor size, and tumor location are presented in Table 1. Notably, all five were intracanalicular tumors 1 cm or smaller. Two of the cases were from an NF2 patient (patient #1) with bilateral tumors.

TABLE 1

General information on the five tumor cases that passed standard ABR analyses.

| PAT-IENT | GENDER | SYMPTOMS | TUMOR SIDE | TUMOR SIZE | TUMOR LOCATION |
|---|---|---|---|---|---|
| 1 | Male | Hearing loss | Right | 0.8 cm | IAC |
|   |      | Hearing loss, tinnitus | Left | 1.0 cm | IAC |
| 2 | Male | Headaches | Left | 0.9 cm | IAC |
| 3 | Male | Hearing loss, dizziness, vertigo | Right | 0.6 cm | IAC |
| 4 | Female | Hearing loss, tinnitus, balance problems | Right | 0.7 cm | IAC |

Standard $IT_5$ Results

Results of the clinical ABR tests, thresholds and the average threshold for four pure-tone frequencies (PTA) are presented in Table 2. In three of the five cases, the $IT_5$ delays were normal. The remaining two cases are from an NF2 patient with bilateral tumors; therefore, the $IT_5$ is an inappropriate measure. The absolute latencies and subjective judgments of waveform morphology appeared normal for all five cases.

TABLE 2

Clinical ABR test results on the five tumor cases that passed standard ABR analyses

| PATIENT | 4-FREQUENCY Threshold/Pure-tone Average (PTA) 0.5, 1, 2, 4 kHz | CLINICAL ABR RESULTS | | |
|---|---|---|---|---|
| | | ABSOLUTE WAVE V LATENCY | INTERAURAL WAVE V LATENCY | WAVEFORM MORPHOLOGY |
| 1 | 10-10-5-10 PTA = 9 | 5.7 ms | N/A | Good |
|   | 5-10-20-55; PTA = 22 | 5.8 ms | N/A | Good |
| 2 | 10-10-5-0; PTA = 6 | 6.2 ms | 0.10 ms | Good |
| 3 | 0-20-20-35; PTA = 19 | 6.0 ms | 0.10 ms | Good |
| 4 | 20-35-40-55; PTA = 36 | 5.9 ms | 0.10 ms | Good |

Standard I–V Delay Results

Figures 9A, 9B:
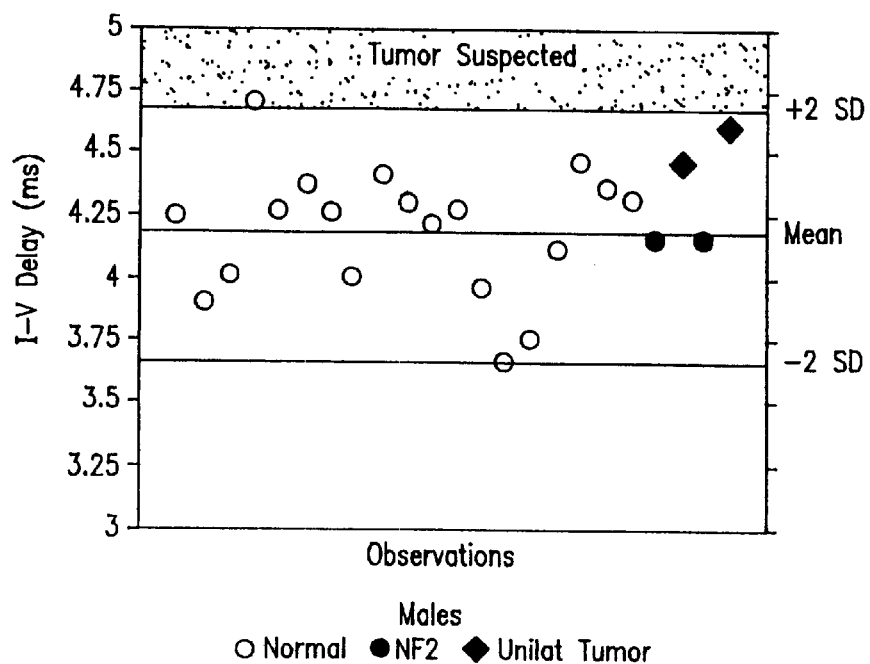
FIGS. 9a and 9b are scatter plots of the I–V delay for both normal hearing subjects and subjects having small acoustic tumors.
Figure 10A:
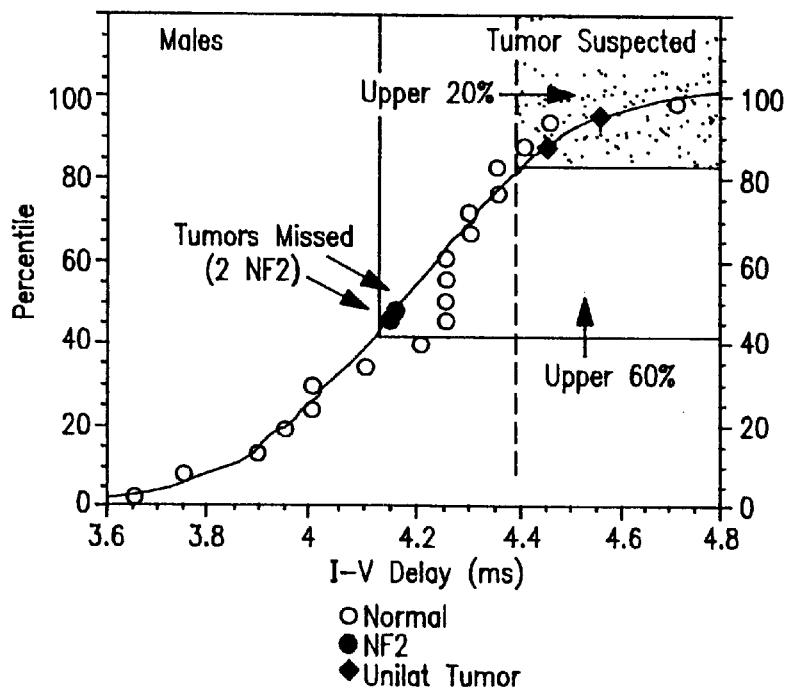
FIGS. 10a and 10b plot the data from FIG. 9 as cumulative percentile curves.
Figure 10B:
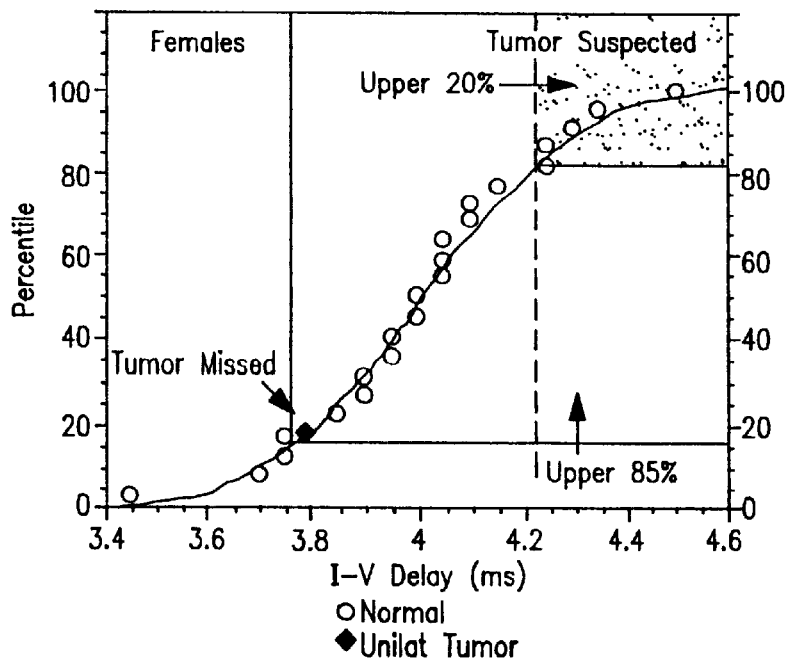

The I–V delays were measurable in all five ears. Since I–V delays are slightly different for males and females, the analyses are performed separately for each gender. A common criterion for suspecting a tumor is a I–V delay that exceeds 2 standard deviations (SDs) from the mean I–V delay [delay>(mean+2 SDs)] for normal-hearing individuals of the same gender. FIGS. 9a and 9b show I–V measurements from males and females, respectively, for both normal-hearing control subjects and the five tumor patients. None of the I–V delays of the five tumor patients fall within the suspected tumor area if a rather stringent criterion of 2 SDs [delay>(mean+2 SDs)] is used. A more reasonable clinical approach to screening is demonstrated in FIGS. 10a and 10b which plot the cumulative percentile curve for the I–V delay for the male and female control groups, respectively. By setting the I–V delay criterion so that 20% of these normal-hearing non-tumor cases would be suspected (shaded areas), detection should improve. For example, in FIG. 10a, only 20% of the males have delays longer than 4.4 ms. For females (FIG. 10b), this criterion is a little over 4.2 ms. Individuals falling within the shaded portion of the curves would be suspected of having a tumor and referred for the more definitive MRI. Only two of the five missed tumor cases would be detected at a cost of imaging 20% of the non-tumor normal-hearing ears. Using the I–V delay to detect all the tumor cases in this series would require imaging nearly 60% of the normal-hearing males and 85% of the normal-hearing females (light gray shaded areas).

Standard Wave V Amplitude

Figure 11A:
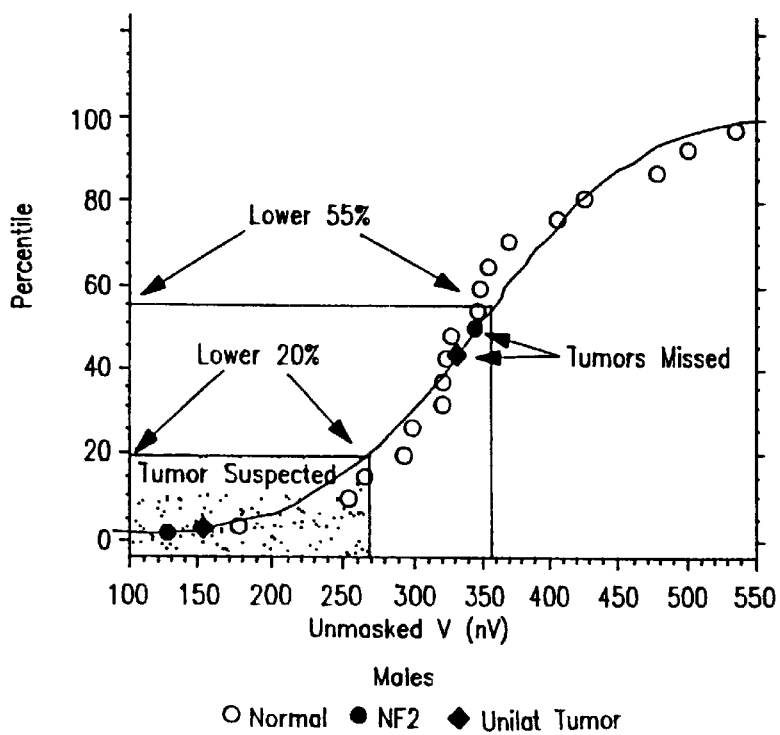
FIGS. 11a and 11b present cumulative percentile curves of standard wave V amplitude measures.
Figure 11B:
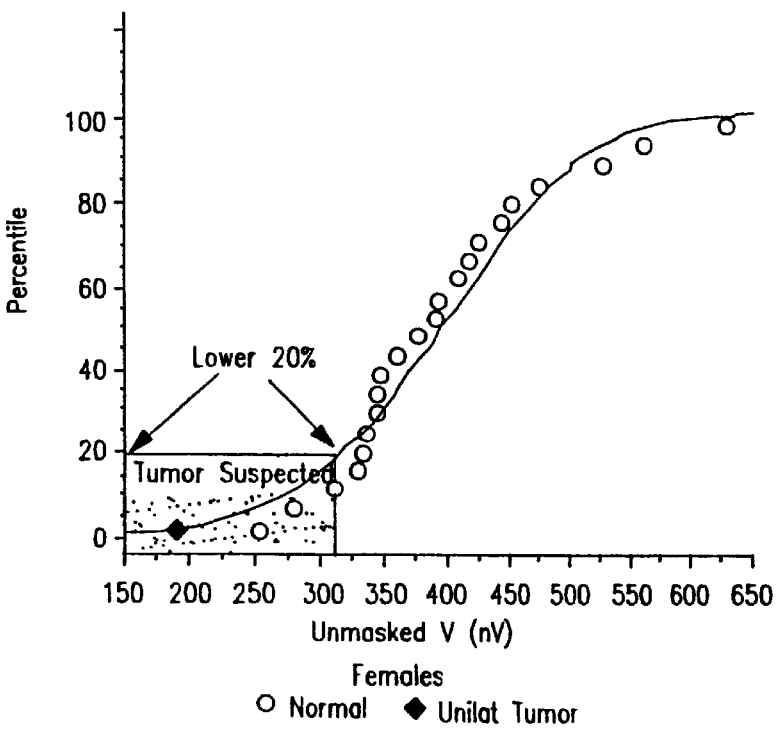

FIGS. 11a and 11b plot the cumulative percentile curve of the control groups for the simple unmasked wave V amplitude measures. By applying the same 20% criterion, three of the five missed tumors would be detected by these simple amplitude measures. This detection is probably better than might be achieved by standard ABR methodology since these amplitude measures have been improved by noise estimation weighting techniques that consistently reduced the residual noise in the averaged waveform to a very low level (20 nV RMS). Even with this technical refinement, 55% of normal-hearing male subjects must be imaged to detect all tumor cases.

Stacked ABR Wave V Amplitude

Figure 12A:
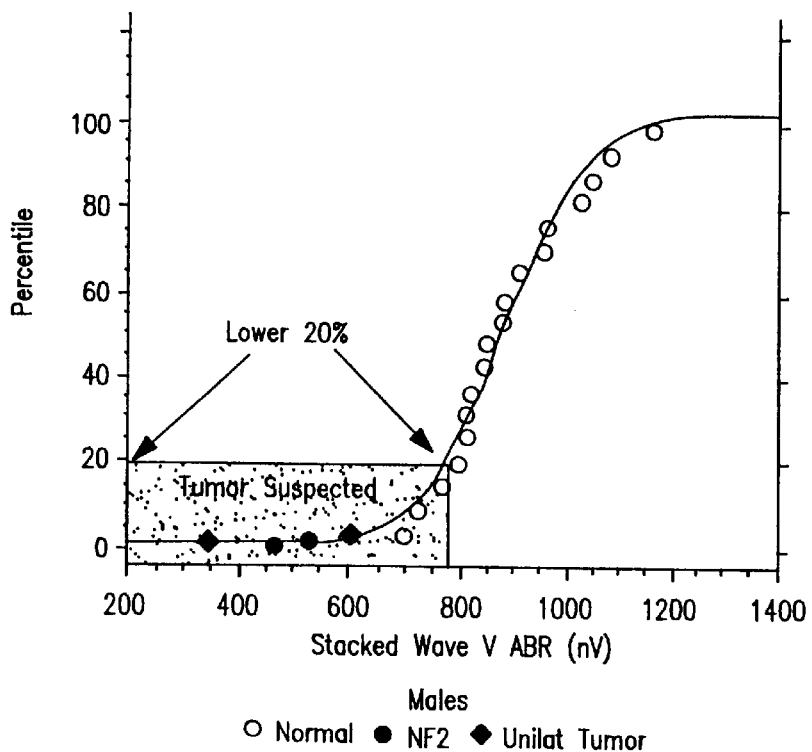
FIGS. 12a and 12b present cumulative percentile curves of stacked wave V amplitude measures.
Figure 12B:
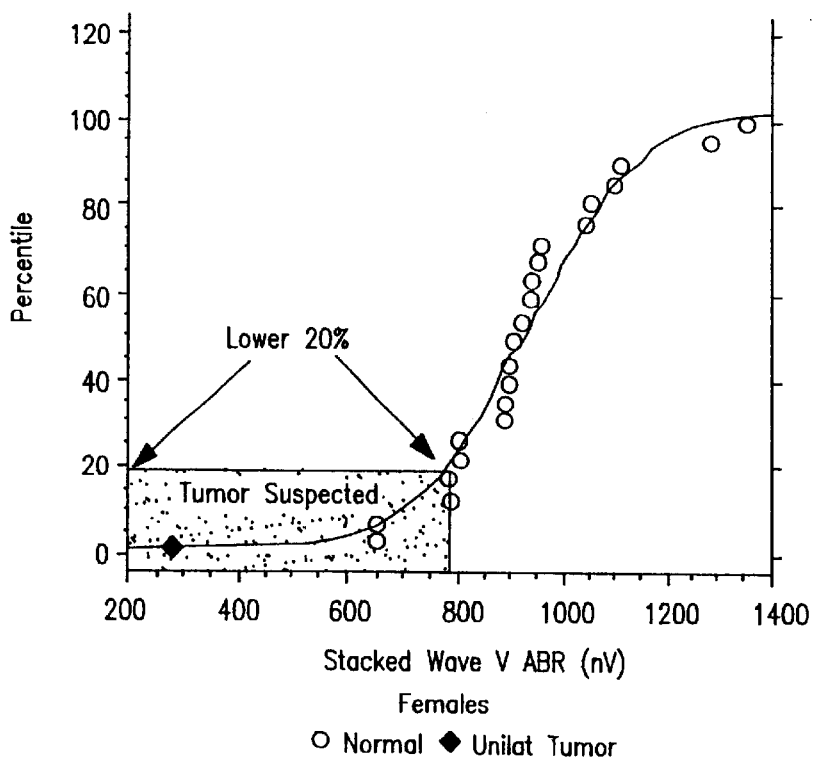
Figure 13A:
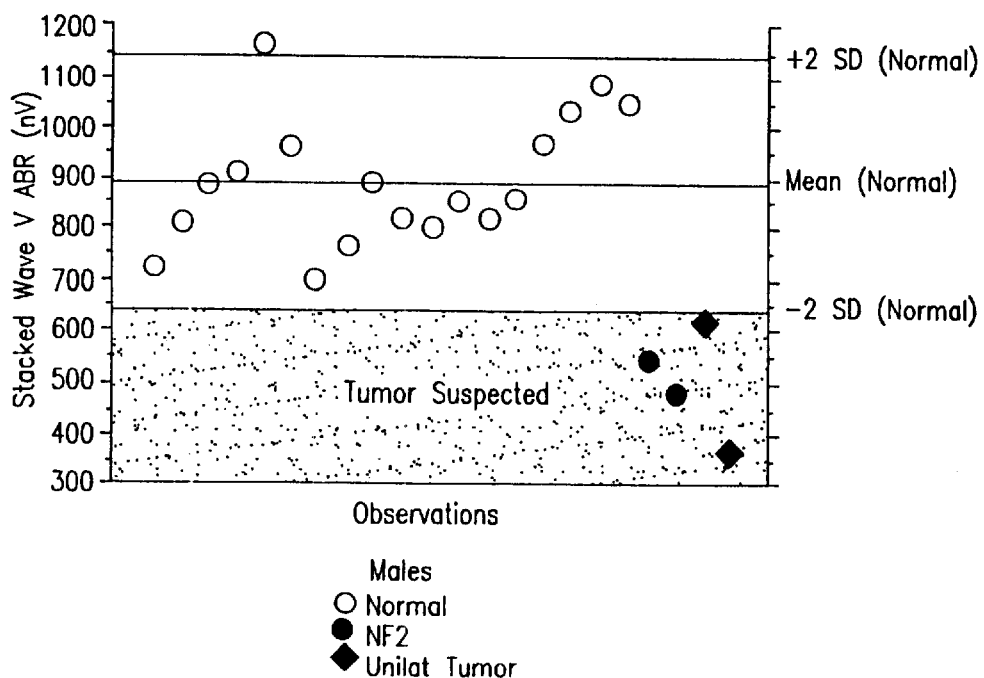
FIGS. 13a and 13b are scatter plots of the stacked wave V amplitude measures.
Figure 13B:
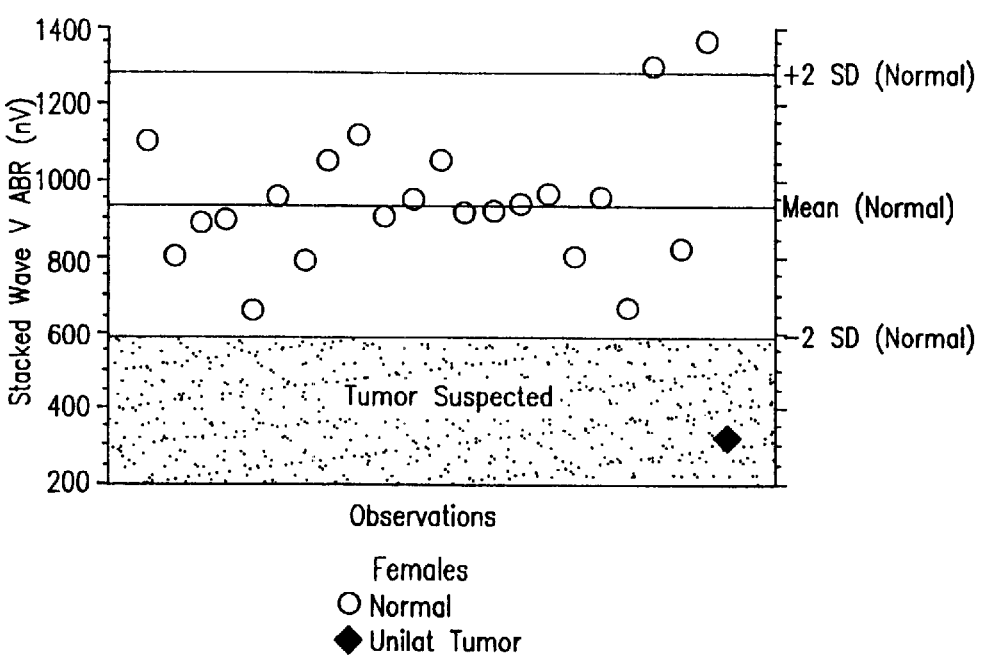

Results using the wave V amplitude of the stacked ABR are shown in FIGS. 12a and 12b for males and females, respectively. By applying the same 20% false positive criterion, all five tumor cases fall well within the "suspected tumor" area of the curves. In fact, for this limited set of data, all five cases fall below the lower 5% of the control values. Thus, in order to detect all five missed tumors, less than 5% of the non-tumor ears in our control group would have been imaged, compared to the nearly 80% and 55% that would have been imaged based on standard latency and amplitude measures respectively. The difference in stacked ABR amplitude between the tumor and the normal-hearing ears is demonstrated in FIGS. 13a and 13b which show that all five tumors are still detected even when applying the rather stringent criterion of 2 SDs. That is, the stacked wave V amplitude for all five tumor cases were more than 2 SDs away from the mean for normal-hearing non-tumor individuals of the same gender.

The Bases for Better Sensitivity of Stacked ABR Amplitude to Small Tumors

Figure 6:
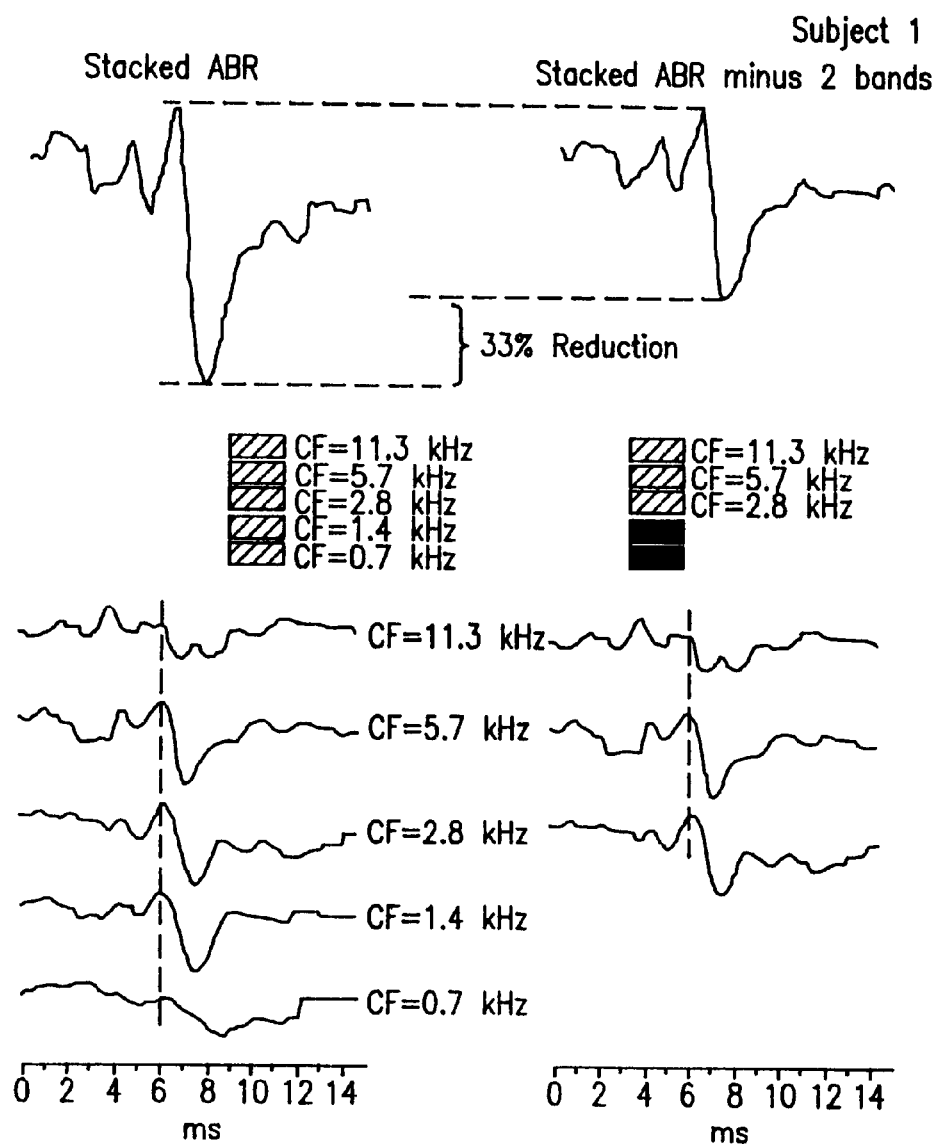
FIG. 6 illustrates the effect of removing the low frequency bands from the stacked ABR for the same subject as shown in FIG. 5.

Experimental application of the present invention has demonstrated that five small tumors missed by standard ABR latency measures were detected with the stacked ABR amplitude measure. In addition, even though a stacked wave V amplitude in the lowest 20% of normal-hearing individuals was the criterion for detection, these five case were in the lowest 5%. Why should this measure be more sensitive to small tumors than the standard latency or amplitude measures? First, the temporal alignment and summation of derived waveforms to form a stacked ABR generates a stacked wave V amplitude that reflects the total synchronous neural response to the stimulus. Thus, unlike for latency measures, the activity of essentially all activated neural elements, rather than a subset, contributes to the stacked amplitude. Therefore, elimination of any significant amount of synchronous neural activity by the tumor will result in a significant reduction in the stacked ABR amplitude (e.g. FIGS. 6 and 8). Due to this sensitivity to the elimination of activity from any neural elements, the stacked wave V amplitude is more sensitive than standard latency and amplitude measures which require compromise of appropriate neural elements.

Improved Specificity Based on Measured Hearing Loss

Since a reduced ABR amplitude may be the result of hearing loss from causes other than a tumor, a threshold based solely on a population of individuals with normal hearing will result in a fairly large number of suspected tumors in patients that suffer from cochlear hearing loss for other reasons. Therefore, it is desirable to establish a threshold for ABR amplitude that takes into account hearing loss experienced by the general population of non-tumor ears.

Figure 16:
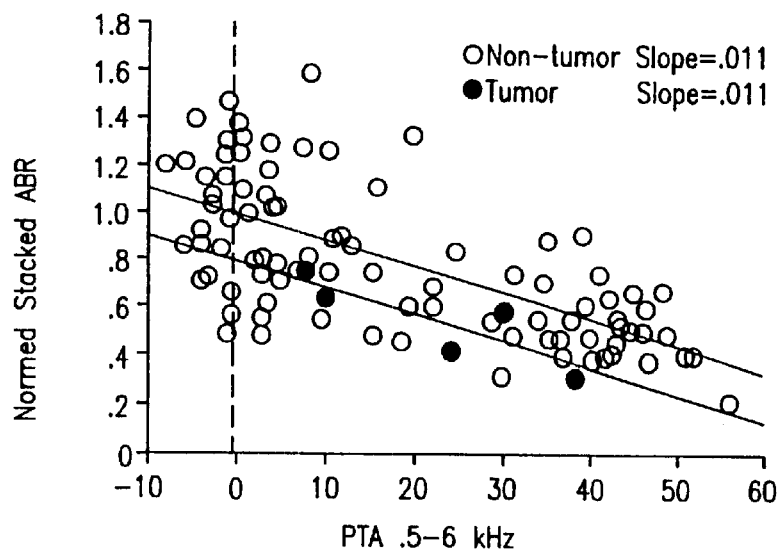
FIG. 16 is a plot of normalized stacked ABR amplitudes versus cochlear hearing loss.

FIG. 16 plots normalized (to the mean of normal-hearing subjects of the same sex) stacked ABR wave V amplitudes against cochlear hearing loss measured with the pure-tone average (PIA) for frequencies in the range of 0.5 to 6 kHz. Data for a non-tumor population of 43 normal-hearing and 69 hearing-impaired subjects are displayed as open circles. The slope of the simple regression line through these data points is 0.011, indicating about a 10% decrease in the normalized stacked ABR amplitude for every 10 dB drop in the PTA. Data for the five tumor patients from Tables 1 and 2 are displayed as filled circles. Even with this limited set of data, the slope is identical to that for the non-tumor ears. This suggests that the impact of hearing loss on stacked ABR amplitude is the same for both tumor and non-tumor ears. However, small tumors cause an additional decrease in the stacked ABR amplitude, thereby separating tumor cases from the non-tumor population. Assuming normal distributions, a diagnostic strategy would be to suspect all cases below the regression curve, i.e., all cases having a stacked ABR amplitude below the mean amplitude of non-tumor individuals having equal PTA hearing loss. This achieves 50% specificity and maintains high sensitivity since all tumors, based on the gathered data, are detected. This would reduce the number of non-tumor patients subjected to further testing, such as MR imaging, by 50% without sacrificing sensitivity.

As mentioned above, PTA is used as a measure of cochlear hearing loss. Since the contribution of each derived band to the stacked ABR is different, it is desirable to weight the PIA accordingly. Thus, for example, if 30% of the stacked ABR amplitude is contributed by a particular derived band, then the pure-tone hearing response for the corresponding frequency region of the cochlea should be assigned a weight of 30% in the overall PTA. Preferred weighting factors for male and female populations are given in Table 3.

TABLE 3

PTA Weighting Factors (5 Octaves)

| OCTAVE CENTER FREQUENCY (KHZ) | % CONTRIBUTION (MALES) | % CONTRIBUTION (FEMALES) |
|---|---|---|
| 11.30 | 14.8 | 13.3 |
| 5.70 | 21.2 | 21.1 |
| 2.80 | 23.2 | 24.2 |
| 1.40 | 21.0 | 23.1 |
| 0.70 | 16.3 | 15.2 |

In many cases, an individual's hearing threshold at frequencies greater than about 6 kHz cannot be measured. In such cases, the preferred weighting factors for computing PTA using only four octaves are given in Table 4.

TABLE 4

PTA weighting Factors (4 Octaves)

| OCTAVE CENTER FREQUENCY (KHZ) | % Contribution (Males) | % Contribution (Females) |
|---|---|---|
| 5.70 | 24.9 | 24.3 |
| 2.80 | 27.2 | 27.9 |
| 1.40 | 24.6 | 26.6 |
| 0.70 | 19.1 | 17.6 |

Inter-Aural Stacked ABR Amplitudes

Figure 7:
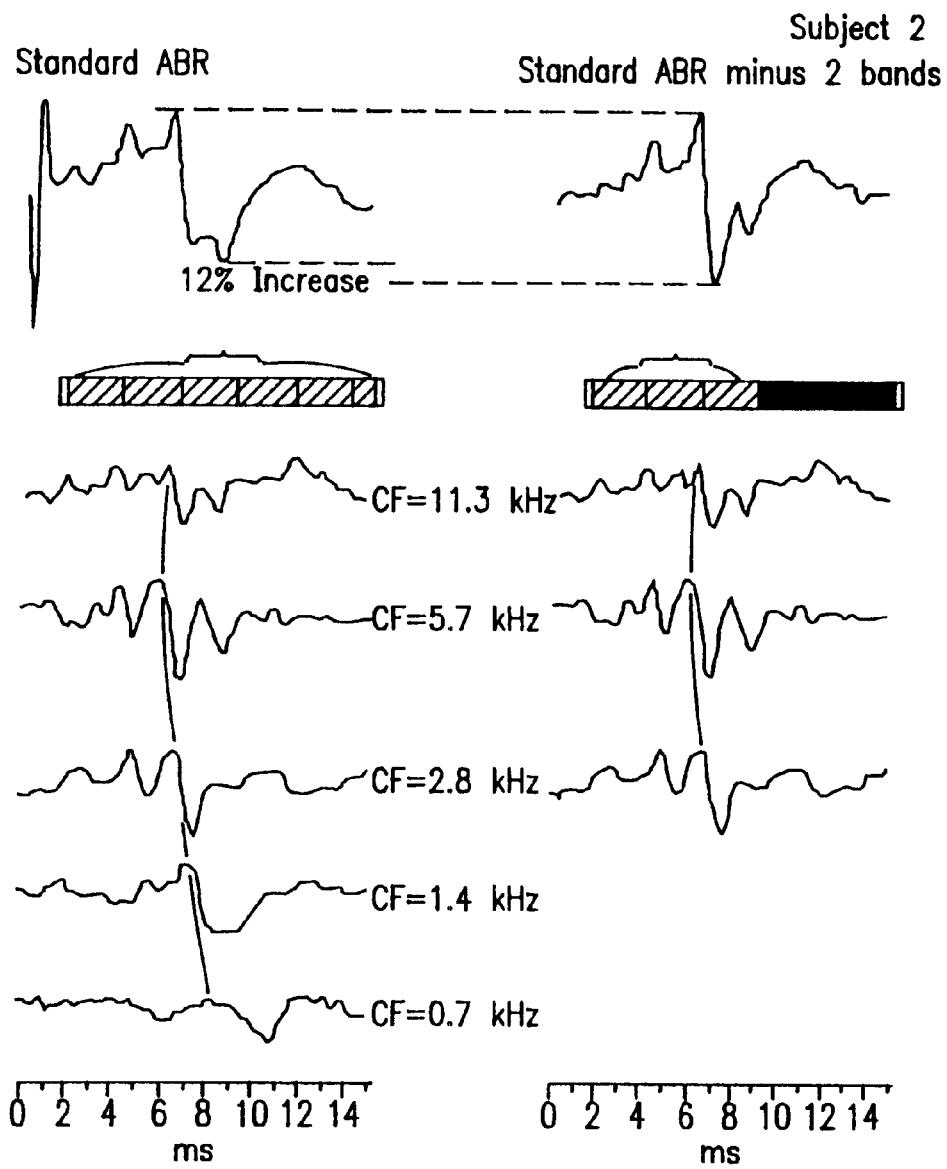
FIG. 7 illustrates a standard ABR in which the wave V amplitude is increased when lower frequency activity is removed.
Figures 14A, 14B:
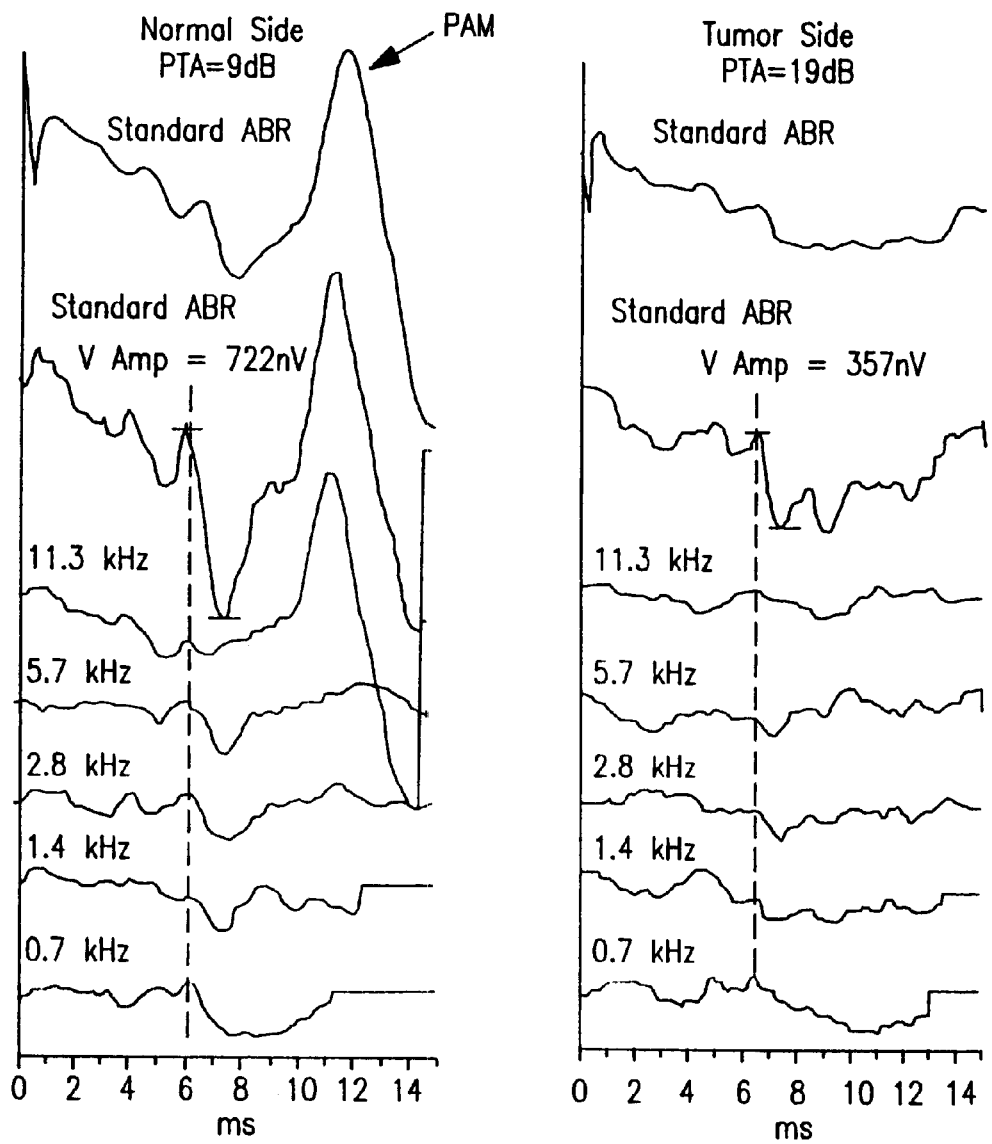
FIGS. 14a and 14b compare the responses from a normal hearing ear and an ear with a tumor in the same patient.

While the variable effects of residual noise and cochlear response times can be minimized to make stacked amplitude measures useful, there is still inherent electrophysiological variability between individuals. This variability could be eliminated in suspected unilateral tumor cases by comparing the stacked wave V amplitudes between the patient's test and normal ears. This is similar to the principle of the $IT_5$ latency measure since comparing the stacked amplitudes between ears within a subject may improve the technique's reliability because intra-subject variability is typically less than inter-subject variability. FIG. 14 illustrates both the standard (top traces both columns) and stacked ABRs for both ears in a unilateral tumor case (patient 3, Table 1). The stacked wave V amplitude for stimulation on the side of the tumor is about half (357 nV) that for the non-tumor side (722 nV). While the standard amplitude for the tumor ear is also significantly reduced in this patient, such a reduction may not always be observed, as demonstrated in FIG. 7. The pure-tone average on the tumor side was 19 dB (Table 2), about 10 dB greater than the normal-hearing side. The nearly 50% reduction of synchronous activity to high level clicks cannot be accounted for by the 10 dB difference in pure-tone averages, which would predict only a 10% reduction in synchronous activity as shown in FIG. 16. Since electrophysiological variability has been reduced by intra-subject testing and the decrease in synchronous activity cannot be attributed totally to the difference in hearing loss, the significant reduction in stacked wave V amplitude must be due, in part, to the tumor.

Figure 17:
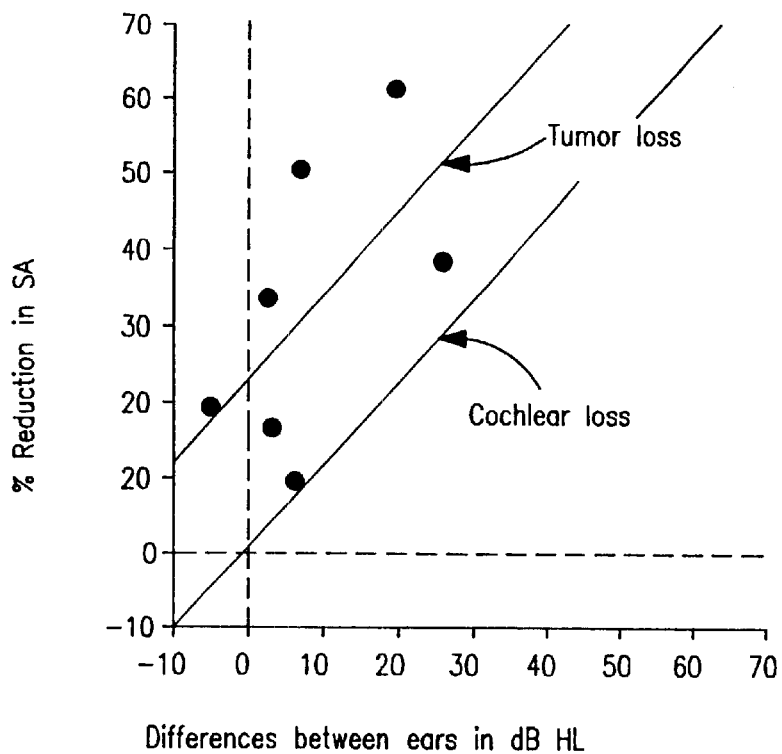
FIG. 17 is a plot of the inter-aural reduction in stacked ABR amplitude for patients with a tumor in one ear.

Referring back to FIG. 16, the stacked ABR amplitude decreases by about 10% for every 10 dB of pure cochlear hearing loss. In addition, the presence of a tumor further reduces the amplitude by about 20%. FIG. 17 plots data for seven tumor cases, showing the percent that the stacked ABR amplitude for the tumor ear is reduced relative to the non-tumor ear as a function of the PIA difference between the ears. If no tumor is present, the data should fall along the lower curve corresponding to pure cochlear hearing loss (10% reduction per 10 dB of difference). Six of the seven cases are well above this curve, indicating a greater degree of reduction than would be expected from pure cochlear hearing loss. Although the limited data do not warrant a regression curve, the data suggest that the stacked ABR amplitude reduction has the same slope in the presence of a tumor, but the tumor contributes an additional 23% reduction in amplitude. Thus, inter-aural comparison appears to provide slightly greater specificity than comparison to a broader population.

Suggested Screening Protocol

For the above-described study of 25 tumor cases, a 100% detection rate was achieved using a combination of standard and stacked ABR methodologies. The standard ABR methodologies ($IT_5$ or I–V delays) detected 20 of the 25 cases but missed 5 small (1 cm or less) intracanalicular tumors. All five of these small tumors were detected by the stacked ABR method. If large (>1 cm) tumors are nearly always detected by standard ABR methods, and since patients with small tumors usually have near-normal hearing, then the following clinical protocol incorporating the stacked ABR method is reasonable and cost efficient.

First, screen with standard ABR measures and request imaging for all patients who fail. This initial screen should detect most tumors greater than 1 cm and about half of the tumors 1 cm or less. In the patients who pass, continue testing with the stacked ABR method to improve detection of tumors smaller than 1 cm; image any who fail. For those patients who pass both the standard and stacked ABR tests, immediate imaging is not indicated. However, continued monitoring is recommended.

Virtually no time is lost in screening with the standard ABR tests first because the unmasked data collected in these tests are used in the stacked ABR method as well. This entire ABR protocol can be completed in one test session.

As discussed above, better sensitivity and specificity can be achieved by:

(1) When possible, use the stacked ABR amplitude from the non-tumor ear as the reference for comparison rather than a normal-hearing population.

(2) For every 10 dB pure-tone average sensory hearing loss, apply a correction factor of 10% reduction to the stacked ABR amplitude.

It will be recognized that the above described invention may be embodied in other specific forms without departing from the spirit or essential characteristics of the disclosure. Thus, it is understood that the invention is not to be limited by the foregoing illustrative details, but rather is to be defined by the appended claims.

What is claimed is:

1. A procedure for diagnosing the presence of a suspected acoustic tumor in a patient's ear comprising:
   (a) determining an average hearing threshold in the suspected ear;
   (b) determining a stacked wave V amplitude for the suspected ear by:
      (i) recording the patient's auditory brainstem response (ABR) to each of a plurality of auditory stimuli;
      (ii) constructing a plurality of derived ABRs representing cochlear responses in a plurality of respective frequency bands;
      (iii) temporally shifting the derived ABRs to align wave V peak amplitudes;
      (iv) computing a stacked ABR by summing the temporally shifted derived ABRs;
      (v) measuring the wave V amplitude of the stacked ABR:
   (c) establishing a wave V amplitude threshold as a function of average hearing threshold;
   (d) diagnosing likely presence of a tumor if the stacked wave V amplitude is below the threshold.

2. The procedure of claim 1 wherein the average threshold is determined by measuring pure-tone hearing thresholds at a plurality of audio frequencies and computing a pure-tone average (PTA) threshold.

3. The procedure of claim 1 wherein the PTA is computed by weighting the pure-tone hearing thresholds with weighting factors corresponding to normal contributions of each derived ABR to the stacked ABR.

4. The procedure of claim 1 wherein the wave V amplitude threshold is established based on data from a population of individuals of the same gender as the patient.

5. The procedure of claim 4 wherein the population of individuals comprises both normal-hearing and hearing-impaired individuals.

6. A procedure for diagnosing the presence of a suspected acoustic tumor in a patient comprising:
   (a) determining an average hearing threshold in each of the patient's ears;
   (b) determining a stacked wave V amplitude for each of the patient's ears by:
      (i) recording the patient's auditory brainstem response (ABR) to each of a plurality of auditory stimuli;
      (ii) constructing a plurality of derived ABRs representing cochlear responses in a plurality of respective frequency bands;
      (iii) temporally shifting the derived ABRs to align wave V peak amplitudes;
      (iv) computing a stacked ABR by summing the temporally shifted derived ABRs;
      (v) measuring the wave V amplitude of the stacked ABR;
   (c) calculating the inter-aural difference in the average hearing thresholds;
   (d) calculating the inter-aural difference in the stacked wave V amplitudes;
   (e) diagnosing likely presence of a tumor if the inter-aural difference in the stacked wave V amplitudes is below a predetermined function of the inter-aural difference in the average hearing thresholds.

7. The procedure of claim 6 wherein the average threshold is determined by measuring pure-tone hearing thresholds at a plurality of audio frequencies and computing a pure-tone average (PTA) threshold.

8. The procedure of claim 6 wherein the PTA is computed by weighting the pure-tone hearing thresholds with weighting factors corresponding to normal contributions of each derived ABR to the stacked ABR.

* * * * *